US00PP17301P3

(12) United States Plant Patent

Way et al.

(10) Patent No.: US PP17,301 P3

(45) Date of Patent: Dec. 26, 2006

(54) 'RIDGEWOOD CHERRY' CULTIVAR

(50) Latin Name: *Prunus avium*
Varietal Denomination: Ridgewood

(75) Inventors: Roger D. Way, Stanley, NY (US); Robert Andersen, Geneva, NY (US); Susan K. Brown, Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 89 days.

(21) Appl. No.: 09/894,311

(22) Filed: Jun. 27, 2001

(65) Prior Publication Data

US 2003/0005495 P1 Jan. 2, 2003

(51) Int. Cl.
*A01H 5/00* (2006.01)

(52) U.S. Cl. ..... Plt./181

(58) Field of Classification Search ..... Plt./181
See application file for complete search history.

*Primary Examiner*—Anne Marie Grunberg
*Assistant Examiner*—Georgia Helmer
(74) *Attorney, Agent, or Firm*—Flynn, Thiel, Boutell & Tanis, P.C.

(57) ABSTRACT

A new and distinct variety of sweet cherry tree, *Prunus avium*, originating as a hybrid seedling of the cross: 'Starks Gold' (unpatented)×'Stella' (unpatented). This new variety is unique from its parents and other sweet cherries varieties because it is late blooming, dark skinned, dark fleshed, and is self-fertile.

2 Drawing Sheets

FIELD OF THE INVENTION

A new and distinct variety of sweet cherry tree originated as a seedling of *Prunus avium* in the breeding program of Cornell University and is hereinafter referred to as 'Ridgewood' sweet cherry. This new variety is unique because this is the latest blooming self-fertile sweet cherry that has been made available to the commercial nursery industry of the United States of America. The flowers are frost tolerant due to both genetic resistance and evasion of frost due to late bloom time; and the fruit is acceptable for fresh market uses.

SUMMARY OF THE INVENTION

This new and distinct variety of sweet cherry was discovered in 1984 by Roger D. Way (retired), a plant breeder at the New York State Agricultural Experiment Station, Geneva, N.Y., a research unit of Cornell University, hereinafter referred to as Geneva Experiment Station. By breeding methodology convention at the Geneva Experiment Station it was designated as NY 13791. This selection was initially assigned Experiment Station Breeding Record Number 75.306, a hybrid population of trees that resulted from hybridizing the varieties 'Starks Gold' (unpatented× 'Stella' (unpatented) in 1975, and this seedling was designated as NY 13791 when it was planted in 1976 as part of a population of 433 siblings possessing the same parentage. The orchard location where the seedling was grown and first noticed was designated as Crittenden Farm, Field Number 30, Row 6, Tree 046. This seedling was first noticed because in 1985 Cornell scientists purposely bagged branches to isolate the flowers from pollinating insect visits and it cropped heavily inside the bag, proving that it was self-fertile; and the fruit were tolerant to rain cracking and rated as being equal in fresh market value to those of the 'Summitt' (unpatented) variety. The new variety has been propagated near Geneva, N.Y. on Mazzard seedling (unpatented), Mahaleb seedling (unpatented), 'Gisela 6' (U.S. Plant Pat. No. 8,954), 'M×M 2' (U.S. Plant Pat. No. 8,194) and 'M×M 60' (U.S. Plant Pat. No. 8,132) rootstocks and remains true to the description herein.

The new variety differs from the parents in that it has dark reddish black skin and flesh in contrast to 'Starks Gold' (unpatented) which has light yellow flesh and yellow and red skin. The new variety differs from 'Stella' (unpatented) in that 'Ridgewood' has a late mid season ripening time and is very cold hardy and frost resistant whereas 'Stella' (unpatented) ripens in early mid season and is very cold and frost tender.

A BRIEF DESCRIPTION OF THE DRAWINGS

The accompanying photographs show typical specimens of the new variety as depicted in color as nearly true as is reasonably possible in color illustrations of this character. These specimens were obtained at the Geneva Experiment Station, Geneva, New York.

Figure 1:
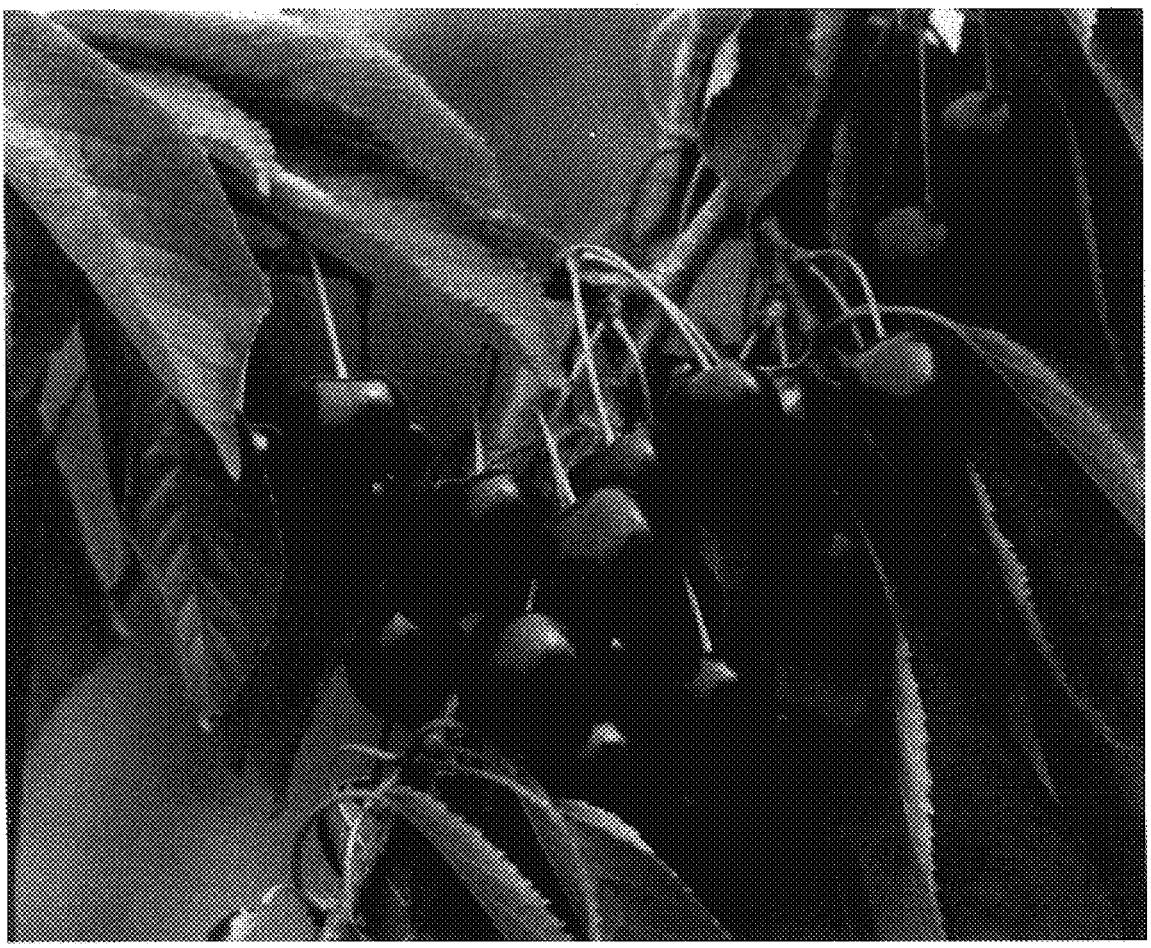

FIG. 1. illustrates the intact fruit and foliage of the new variety at maturity.

Figure 2:
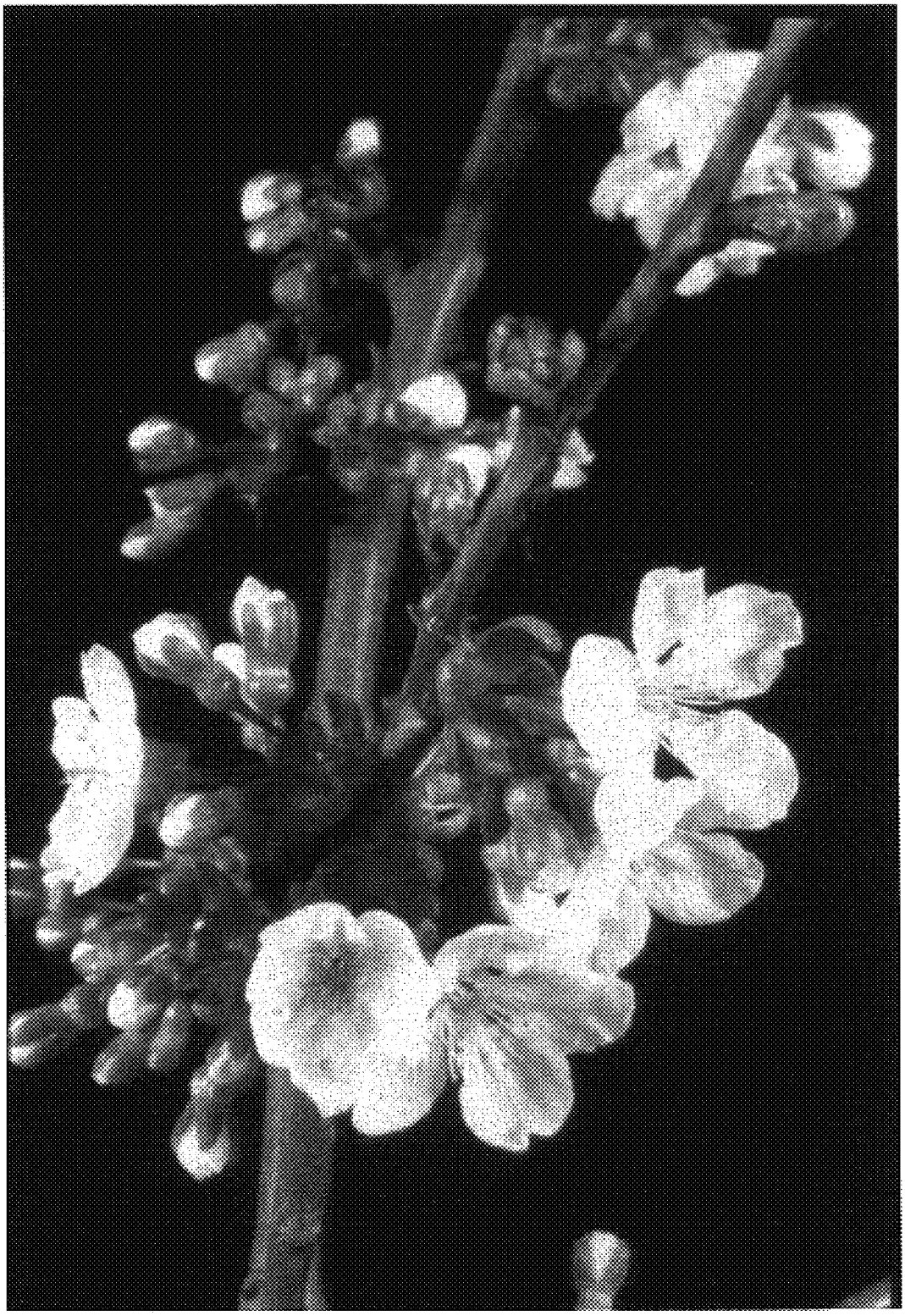

FIG. 2. illustrates the blossoms of the new variety.

A BOTANICAL DESCRIPTION OF THE PLANT

A detailed description of the 'Ridgewood cherry' cultivar follows using The Royal Horticultural Society of London Colour Chart for color identification except where general color terms are sufficient.

Parentage: A hybrid seedling of the cross: 'Starks Gold' (unpatented)×'Stella' (unpatented). Locality of the original discovery and observations is the Crittenden Farm Research Orchard Number 30, Row 6, tree 046 (assigned the designation NY 13791), Geneva Experiment Station, Geneva, N.Y., U.S.A.

Tree:

*Age of specimen.*—25 years old.

*Height.*—4.5 M.

*Width.*—4.5 M.

*Size.*—73 cm in diameter at 100 cm above ground level.

*Vigor.*—Medium.

*Density.*—Medium.

*Form.*—Spreading, laterals are pendant to about the same degree as 'Starks Gold' (unpatented), the female parent of the new variety.

*Production.*—Heavy, 200 to 250 pounds per season per tree on seedling rootstocks.

*Bearing.*—Annual on spurs and on 2 to 4 bud positions located at the base of one year old shoots.

*Disease resistance.*—Similar to 'Stella' (unpatented) in tolerance to brown rot fungus of the blossoms and fruit (rated 6 at Geneva on scale of 1, as worst, to 9, as best); also similar to 'Stella' (unpatented) in tolerance to bacterial canker of the tree and fruit (rated 6 at Geneva on scale of 1, as worst, to 9 as best); highly tolerant of black knot fungus of the wood.

*Cold hardiness.*—Good, crops regularly in test orchards in commercial fruit districts of New York and Michigan.

*Frost tolerance.*—Excellent (rated 8 at Geneva on scale of 1, as worst, to 9, as best).

*Graft compatibility.*—Good, produces compatible graft unions with Mazzard (unpatented) seedling, Mahaleb seedling (unpatented), 'Gisela 6' (U.S. Plant Pat. No. 8,954), 'M×M 2' (U.S. Plant Pat. No. 8,194) and 'M×M 60' (U.S. Plant Pat. No. 8,132) cherry rootstocks.

Trunk:

*Size.*—70 cm in diameter at 100 cm above ground level.

*Surface.*—Bark is smooth with prominent lenticels.

*Bark color.*—Grayed Purple 183 A where directly exposed to the sun.

*Lenticels.*—Grayed Orange 167 A, varying in length from 1.5 to 5.0 cm and width from 0.3 to 0.7 cm, prominent, horizontal, elliptical.

Branches:

*1 year old branches.*—Average length 42 cm, width 4 cm, internode distance 35 cm, color Grayed Orange 166c.

*2 year old branches*—Average length 45 cm, width 6 cm, internode distance 32 cm, color Grayed Orange 166A.

*Lenticils.*—Few, scattered, color Grayed Yellow 161C.

Vegetative buds:

*Placement.*—At bud positions 4 and higher numbered from the base of new growth, and at tip of each fruit spur.

*Appearance.*—Pointed and flatter than flower buds on previous season's annual growth of shoots.

*Color.*—Yellow Green 144 D.

Leaves:

*Size.*—9.0 to 11.5 cm in length, 5.5 to 6.5 cm in width with.

*Form.*—Symmetrical halves on both sides of central axis.

*Thickness.*—Medium.

*Texture.*—Crisp, leathery.

*Pubescence.*—None on either surface.

*Margin.*—Serrations regular and bluntly pointed.

*Adaxile surface.*—Green 137A.

*Abaxile surface.*—Yellow Green 148C.

*Veination.*—Pinnate.

*Vein color.*—Adaxial Yellow Green 144 D, abaxial Yellow Green 144 B.

*Petiole.*—6.0 to 6.5 cm in length.

*Petiole color.*—Red Purple 59 A.

*Petiole groove.*—Narrow.

*Glands.*—1 to 2 on petiole, bluntly globose, length 1.5 to 1.75 mm, width 1 to 1.25 mm, color Orange 28 A.

Flower buds:

*Size.*—Length 12 cm, width 5 cm.

*Form.*—Elongated oval.

*Color.*—Green 143B.

*Peduncle.*—Length 4.8 to 5.25 mm, width 0.4 mm, Green 143 B.

*Number of buds per spur.*—3 to 7, average of 5.

Flowers:

*Blooming period.*—Late, May 1 to May 5 in Geneva, N.Y.

*Presentation.*—Non-showy white.

*Fragrance.*—Sweet, flowery.

*Fertility.*—Self-fertile.

*Pollen.*—Present, plentiful, good pollen source for pollenizing all other sweet cherries that bloom at the late-season sequence, color Yellow 13A.

*Corolla diameter.*—32 mm.

*Number of flowers per cluster.*—5 to 9.

*Petals.*—Single, round, length 10 mm, width 10 mm, 5 in number, slightly overlapping, margin slightly ruffled, soft texture, White 155D.

*Peduncle.*—Length 4.8 to 5.25 mm, width 0.4 mm, Green 143 B.

*Filament.*—Length 8 mm, width 0.1 mm, White 155 D.

*Anther.*—Profuse pollen, Yellow 13 A.

*Sepals.*—5 in number, Green 143 B, bluntly ovate in shape.

Fruit:

*Maturity when described.*—Commercial ripeness, 17 degrees brix.

*Date of first picking.*—Mid-late season ripening, July 10th to July 15 at Geneva, N.Y.

*Size.*—Weight 9 g, length 3.0 cm, width 2.8 cm.

*Form.*—Round-oblong appearance; fruit tapers from widest dimension on cheeks toward stigmatic scar and gives the appearance of slightly heart shape.

*Stem cavity.*—Wide, not prone to concentric cracks from rain settling in the cavity.

*Stem.*—Length 38 mm, width 1.5 mm, color Green 143B.

Skin:

*Thickness.*—Medium.

*Tendency to crack.*—Similar to Stella, rated as 7 at Geneva (1, worst to 9 best); may split on shoulders in high rainfall seasons.

*Color.*—Grayed Purple 187B.

*Flavor.*—Good.

Flesh:

*Texture.*—Medium firm, rated as 6 at Geneva (1, worst to 9 best).

*Acidity.*—Medium high until sugar level gets to above 15 degrees brix.

*Flavor.*—Good.

*Aroma.*—Present, pleasing.

*Color.*—Grayed Purple 187D.

*Coloration in the pit cavity.*—Same as flesh.

*Juice.*—Abundant, sweet.

*Eating quality.*—Good when mature to above 16 degrees brix, slightly acid if eaten when immature.

Stone:

*Size.*—1.5 cm in length, 1.25 cm in width at widest point near the center, 0.75 cm in width at widest point of the flatter direction.

*Form.*—Slightly oblong.

*Sides.*—Ridges, 3 to 5 in number, with varying amounts of encircling the suture side of the pit.

*Type.*—Freestone at commercial maturity.

*Tendency to crack.*—Non-existent.

Use: Fresh market; may become popular for commercial orchardists to use as pollenizer because it is universally compatible with all other sweet cherry varieties and has a uniquely late bloom time which matches that of several important new sweet cherry varieties that are entering commerce in the United States of America which require cross pollinization. May become popular for home orchards if lawn/garden space is limited because its self-fertile trait allows successful cultivation of just one sweet cherry tree and 'Ridgewood' is both frost tolerant and self-fertile.

I claim:

1. A new and distinct variety of sweet cherry tree, named Ridgewood, substantially as herein shown and described, characterized as to novelty by the unique combination of late emerging, self-fertile flowers and good frost hardiness of the flower buds and possessing, fresh market, eating quality, and shipping/handling attributes that meet grade standards for this fruit.

* * * * *